United States Patent
Oh et al.

(10) Patent No.: US 11,795,154 B2
(45) Date of Patent: Oct. 24, 2023

(54) METHOD FOR THE SYNTHESIS OF 2,5-FURANDICARBOXYLIC ACID

(71) Applicants: SAMYANG CORPORATION, Seoul (KR); RESEARCH & BUSINESS FOUNDATION SUNGKYUNKWAN UNIVERSITY, Suwon-si (KR)

(72) Inventors: Chun Rim Oh, Seoul (KR); Deuk Rak Lee, Daejeon (KR); Won Jung Lee, Daejeon (KR); Chi Wan Lee, Daejeon (KR); Ji Eun Choi, Seongnam-si (KR); Young Sug Kim, Cheongju-si (KR); Jung Woon Yang, Anyang-si (KR); Tae Woo Lee, Suwon-si (KR)

(73) Assignees: SAMYANG CORPORATION, Seoul (KR); RESEARCH & BUSINESS FOUNDATION SUNGKYUNKWAN UNIVERSITY, Suwon-si (KR)

( * ) Notice: Subject to any disclaimer, the term of this patent is extended or adjusted under 35 U.S.C. 154(b) by 149 days.

(21) Appl. No.: 17/440,360

(22) PCT Filed: Mar. 20, 2020

(86) PCT No.: PCT/KR2020/003845
§ 371 (c)(1),
(2) Date: Sep. 17, 2021

(87) PCT Pub. No.: WO2020/190080
PCT Pub. Date: Sep. 24, 2020

(65) Prior Publication Data
US 2022/0162179 A1    May 26, 2022

(30) Foreign Application Priority Data

Mar. 20, 2019 (KR) .................. 10-2019-0031921
Jan. 28, 2020 (KR) .................. 10-2020-0009897

(51) Int. Cl.
*C07D 307/68* (2006.01)

(52) U.S. Cl.
CPC .................. *C07D 307/68* (2013.01)

(58) Field of Classification Search
CPC .................. C07D 307/68; C07D 307/46
USPC ....................................... 549/256
See application file for complete search history.

(56) References Cited

FOREIGN PATENT DOCUMENTS

| | | |
|---|---|---|
| CN | 104888863 A | 9/2015 |
| CN | 105037303 A | 11/2015 |
| CN | 107325065 A | 11/2017 |
| CN | 107987041 A | 5/2018 |
| KR | 10-2018-0090840 A | 8/2018 |
| KR | 10-2018-0106865 A | 10/2018 |
| KR | 10-2018-0107143 A | 10/2018 |

OTHER PUBLICATIONS

Zhang et al., "A new approach for the aerobic oxidation of 5-hydroxymethylfurfural to 2,5-furandicarboxylic acid without using transition metal catalysts," Journal of Energy Chemisty, vol. 27, 2018, (Available online Jun. 3, 2017), pp. 243-249.

*Primary Examiner* — Taylor V Oh
(74) *Attorney, Agent, or Firm* — Birch, Stewart, Kolasch & Birch, LLP

(57) ABSTRACT

The present invention relates to a method for the synthesis of 2,5-furandicarboxylic acid, and more specifically, the present invention relates to a more efficient and economical method capable of preparing 2,5-furandicarboxylic acid having various functions with high purity and high yield, even without using a transition metal catalyst.

5 Claims, No Drawings

METHOD FOR THE SYNTHESIS OF 2,5-FURANDICARBOXYLIC ACID

TECHNICAL FIELD

The present invention relates to a method for the synthesis of 2,5-furandicarboxylic acid, and more specifically, the present invention relates to a more efficient and economical method capable of preparing 2,5-furandicarboxylic acid having various functions with high purity and high yield, even without using a transition metal catalyst.

BACKGROUND ART 2,5-furandicarboxylic acid (FDCA) is a very useful material which has various functions and is widely used in packaging industries (polyamides, polyesters, polyurethanes, etc.), automobiles, pharmaceutical field, fine chemicals, etc. In addition, because polyethylene furanoate (PEF), a bio plastic which has been developed as an alternative to polyethylene terephthalate (PET), can be obtained from 2,5-furandicarboxylic acid (FDCA), the value of research therefor is increasing.

A method for obtaining 2,5-furandicarboxylic acid (FDCA) by oxidizing 5-hydroxymethylfurfural (HMF) has been known. However, in such a conventional method, since the reaction is conducted by using an excessive equivalent amount of nitric acid as the oxidizing agent under very strict and delicate conditions, generation of undesired byproducts cannot be avoided. Thereafter, methods for chemoselective synthesis of 2,5-furandicarboxylic acid (FDCA) by utilizing various transition metals such as gold, platinum, palladium, titanium, etc. and using oxygen as an oxidizing agent have been developed (for example, Korean Laid-open Patent Publication Nos. 10-2018-0090840 and 10-2018-0107143). However, such methods are hard to industrialize since they use expensive transition metal catalysts and the reactions should be conducted at high temperature or under high pressure.

Therefore, it has been required to develop a method capable of preparing 2,5-furandicarboxylic acid (FDCA) from 5-hydroxymethylfurfural (HMF) using oxygen (or air) as an oxidizing agent with high purity and high yield, even without using a transition metal catalyst.

DISCLOSURE OF INVENTION

Technical Problem

The present invention is intended to resolve the above-stated problems of the prior arts, and has an object of providing a method capable of preparing 2,5-furandicarboxylic acid (FDCA) from 5-hydroxymethylfurfural (HMF) with high purity and high yield, even without using a transition metal catalyst, through a chemoselective oxidation reaction based on eco-friendly protocols of alkali metal (or alkaline-earth metal) compound and oxygen (or air).

Solution to Problem

In order to resolve the above-stated problems, the present invention provides a method for preparing 2,5-furandicarboxylic acid from 5-hydroxymethylfurfural through a chemoselective oxidation reaction, wherein the chemoselective oxidation reaction is conducted with using oxygen or air as an oxidizing agent, in the presence of a promotor which is an alkali metal or alkaline-earth metal compound.

Advantageous Effects of Invention

According to the present invention, it is possible to prepare highly pure 2,5-furandicarboxylic acid (FDCA)—which is used widely and advantageously in various fields such as packaging industries, automobiles, pharmaceutical field, fine chemicals, etc.—from 5-hydroxymethylfurfural (HMF) by a more economical, efficient and eco-friendly method.

BEST MODE FOR CARRYING OUT THE INVENTION

The present invention is explained in more detail below.

The present invention relates to a method for preparing 2,5-furandicarboxylic acid (FDCA) through a chemoselective oxidation reaction oxidizing the alcohol functional group and aldehyde functional group in the molecule of 5-hydroxymethylfurfural (HMF), as shown in the following Reaction Scheme 1:

[Reaction Scheme 1]

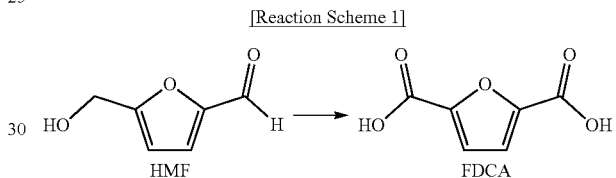

In the method for preparing 2,5-furandicarboxylic acid of the present invention, the chemoselective oxidation reaction is conducted in the presence of a promotor which is an alkali metal or alkaline-earth metal compound.

In an embodiment, the alkali metal can be lithium, sodium, potassium, rubidium, cesium or a combination thereof, and the alkaline-earth metal can be barium, magnesium or a combination thereof.

In an embodiment, the alkali metal or alkaline-earth metal compound used as a promotor can be represented by the following Formula 1:

MOR    [Formula 1]

In the above Formula 1, M is an alkali metal or alkaline-earth metal; and R is an alkyl group, aryl group, alkylaryl group or arylalkyl group.

More concretely, in the above Formula 1, R can be $(C_1 \sim C_{10})$alkyl group, $(C_6 \sim C_{10})$aryl group, $(C_1 \sim C_{10})$alkyl$(C_6 \sim C_{10})$aryl group or $(C_6 \sim C_{10})$aryl$(C_1 \sim C_{10})$alkyl group, and still more concretely, R can be $(C_1 \sim C_6)$alkyl group, $(C_6)$aryl group, $(C_1 \sim C_6)$alkyl$(C_6)$aryl group or $(C_6)$aryl$(C_1 \sim C_6)$alkyl group.

According to the present invention, 2,5-furandicarboxylic acid (FDCA) can be prepared from 5-hydroxymethylfurfural (HMF) with high purity and high yield, even without using expensive transition metal catalyst. Therefore, in a preferable embodiment of the method for preparing 2,5-furandicarboxylic acid of the present invention, no transition metal catalyst is used.

In the method for preparing 2,5-furandicarboxylic acid of the present invention, the chemoselective oxidation reaction can be conducted in various solvents.

The solvent can be water, organic solvent or a combination thereof, and the organic solvent can be non-polar organic solvent, polar protic organic solvent, polar aprotic organic solvent, or a combination thereof.

In an embodiment, the solvent can be water, normal propanol, isopropanol, normal butanol, tert-butanol, tert-amyl alcohol, tetrahydrofuran, 1,4-dioxane, dichloromethane, 1,2-dichloroethane, chlorobenzene, acetonitrile, dimethyl sulfoxide, N,N-dimethylformamide, N,N-dimethylacetamide, benzene, toluene, or a mixture of two or more thereof.

In an embodiment, the promotor which is an alkali metal or alkaline-earth metal compound (for example, alkoxide) can be used in an amount of from 1 to 10 equivalents, based on 5-hydroxymethylfurfural (HMF), and in order to obtain more efficient yield, preferably used in an amount of from 3 to 4 equivalents, based on 5-hydroxymethylfurfural (HMF).

In an embodiment, the chemoselective oxidation reaction can be conducted at a temperature of from 20° C. to 100° C., more concretely, conducted at a temperature of from 20° C. to 60° C. preferably, and more concretely, conducted at a temperature of from 40° C. to 60° C. preferably.

In an embodiment, the chemoselective oxidation reaction can be conducted under condition of 1 to 10 atmospheres, more concretely, conducted at 3 to 5 atmospheres preferably, and more concretely, conducted at 1 to 2 atmospheres preferably.

Since the alkali metal or alkaline-earth metal compound used as a promotor and oxygen or air used as an oxidizing agent in the method for preparing 2,5-furandicarboxylic acid of the present invention themselves have high reactivity, even if the chemoselective oxidation reaction is conducted under relatively low temperature condition (for example, about 40° C.) and relatively low pressure condition (for example, 2 atmospheres), 2,5-furandicarboxylic acid can be prepared with good yield. Therefore, it can be said that the method for preparing 2,5-furandicarboxylic acid of the present invention is very useful in industrialization for mass production.

The present invention is explained in more detail through the following Examples and Comparative Examples. However, the scope of the present invention is not limited thereby in any manner.

EXAMPLES

In the following Examples 1 to 4, the used solvent was tert-butanol, the used promotors were sodium tert-butoxide, sodium tert-amylate, sodium ethoxide and sodium methoxide, respectively, and the reactions were conducted at a reaction temperature of about 30° C. under atmospheric oxygen condition for about 1 day.

In the following Examples 5 to 8, the used solvent was tert-butanol, the used promotors were lithium tert-butoxide, potassium tert-butoxide, magnesium tert-butoxide and barium tert-butoxide, respectively, and the reactions were conducted at a reaction temperature of about 30° C. under atmospheric oxygen condition for about 1 day.

In the following Examples 9 to 23, the used solvents were tetrahydrofuran, 1,4-dioxane, dichloromethane, 1,2-dichloroethane, chlorobenzene, acetonitrile, dimethyl sulfoxide, N,N-dimethylformamide, benzene, toluene, normal butanol, tert-amyl alcohol, N,N-dimethylacetamide, isopropanol and normal propanol, respectively, the used promotor was sodium tert-butoxide, and the reactions were conducted at a reaction temperature of about 25° C. under atmospheric oxygen condition for about 1 day.

In the following Examples 24 to 27, the used solvents were normal butanol and tert-butanol, the used promotor was sodium tert-butoxide, and the reactions were conducted at a reaction temperature of 45° C. and 55° C., respectively, under atmospheric oxygen condition for about 1 day.

Example 1

At 30° C., 3 mL of tert-butanol was added to sodium tert-butoxide (3 equivalents) and then stirred for 5 minutes. 5-Hydroxymethylfurfural (HMF, 0.5 mmol) was added thereto, and the atmosphere was changed to oxygen, and then the mixture was stirred at room temperature for 1 day. To the resulting mixture, a small amount of distilled water was added to terminate the reaction, and the acidity (pH) of the mixture was lowered to 1 with 1N HCl solution, and then the mixture was concentrated. The residue was purified through seed crystals to obtain 2,5-furandicarboxylic acid (FDCA) with 98% yield.

$^1$H NMR (500 MHz, DMSO-$d_6$): δ 13.62 (br, 2H), 7.29 (s, 2H)

$^{13}$C NMR (125 MHz, DMSO-$d_6$): δ 158.91, 147.04, 118.40

Example 2

At 30° C., 3 mL of tert-butanol was added to sodium tert-amylate (3 equivalents) and then stirred for 5 minutes. 5-Hydroxymethylfurfural (HMF, 0.5 mmol) was added thereto, and the atmosphere was changed to oxygen, and then the mixture was stirred at room temperature for 1 day. To the resulting mixture, a small amount of distilled water was added to terminate the reaction, and the acidity (pH) of the mixture was lowered to 1 with 1N HCl solution, and then the mixture was concentrated. The residue was purified through seed crystals to obtain 2,5-furandicarboxylic acid (FDCA) with 89% yield.

$^1$H NMR (500 MHz, DMSO-$d_6$): δ 13.62 (br, 2H), 7.29 (s, 2H)

$^{13}$C NMR (125 MHz, DMSO-$d_6$): δ 158.91, 147.04, 118.40

Example 3

At 30° C., 3 mL of tert-butanol was added to sodium ethoxide (3 equivalents) and then stirred for 5 minutes. 5-Hydroxymethylfurfural (HMF, 0.5 mmol) was added thereto, and the atmosphere was changed to oxygen, and then the mixture was stirred at room temperature for 1 day. To the resulting mixture, a small amount of distilled water was added to terminate the reaction, and the acidity (pH) of the mixture was lowered to 1 with 1N HCl solution, and then the mixture was concentrated. The residue was purified through seed crystals to obtain 2,5-furandicarboxylic acid (FDCA) with 75% yield.

$^1$H NMR (500 MHz, DMSO-$d_6$): δ 13.62 (br, 2H), 7.29 (s, 2H)

$^{13}$C NMR (125 MHz, DMSO-$d_6$): δ 158.91, 147.04, 118.40

Example 4

At 30° C., 3 mL of tert-butanol was added to sodium methoxide (3 equivalents) and then stirred for 5 minutes. 5-Hydroxymethylfurfural (HMF, 0.5 mmol) was added thereto, and the atmosphere was changed to oxygen, and then the mixture was stirred at room temperature for 1 day. To the resulting mixture, a small amount of distilled water was added to terminate the reaction, and the acidity (pH) of the mixture was lowered to 1 with 1N HCl solution, and then the mixture was concentrated. The residue was purified through seed crystals to obtain 2,5-furandicarboxylic acid (FDCA) with 56% yield.

$^{1}$H NMR (500 MHz, DMSO-$d_6$): δ 13.62 (br, 2H), 7.29 (s, 2H)

$^{13}$C NMR (125 MHz, DMSO-$d_6$): δ 158.91, 147.04, 118.40

Example 5

At 30° C., 3 mL of tert-butanol was added to lithium tert-butoxide (3 equivalents) and then stirred for 5 minutes. 5-Hydroxymethylfurfural (HMF, 0.5 mmol) was added thereto, and the atmosphere was changed to oxygen, and then the mixture was stirred at room temperature for 1 day. To the resulting mixture, a small amount of distilled water was added to terminate the reaction, and the acidity (pH) of the mixture was lowered to 1 with 1N HCl solution, and then the mixture was concentrated. The residue was purified through seed crystals to obtain 2,5-furandicarboxylic acid (FDCA) with 88% yield.

$^{1}$H NMR (500 MHz, DMSO-$d_6$): δ 13.62 (br, 2H), 7.29 (s, 2H)

$^{13}$C NMR (125 MHz, DMSO-$d_6$): δ 158.91, 147.04, 118.40

Example 6

At 30° C., 3 mL of tert-butanol was added to potassium tert-butoxide (3 equivalents) and then stirred for 5 minutes. 5-Hydroxymethylfurfural (HMF, 0.5 mmol) was added thereto, and the atmosphere was changed to oxygen, and then the mixture was stirred at room temperature for 1 day. To the resulting mixture, a small amount of distilled water was added to terminate the reaction, and the acidity (pH) of the mixture was lowered to 1 with 1N HCl solution, and then the mixture was concentrated. The residue was purified through seed crystals to obtain 2,5-furandicarboxylic acid (FDCA) with 92% yield.

$^{1}$H NMR (500 MHz, DMSO-$d_6$): δ 13.62 (br, 2H), 7.29 (s, 2H)

$^{13}$C NMR (125 MHz, DMSO-$d_6$): δ 158.91, 147.04, 118.40

Example 7

At 30° C., 3 mL of tert-butanol was added to magnesium tert-butoxide (3 equivalents) and then stirred for 5 minutes. 5-Hydroxymethylfurfural (HMF, 0.5 mmol) was added thereto, and the atmosphere was changed to oxygen, and then the mixture was stirred at room temperature for 1 day. To the resulting mixture, a small amount of distilled water was added to terminate the reaction, and the acidity (pH) of the mixture was lowered to 1 with 1N HCl solution, and then the mixture was concentrated. The residue was purified through seed crystals to obtain 2,5-furandicarboxylic acid (FDCA) with 75% yield.

$^{1}$H NMR (500 MHz, DMSO-$d_6$): δ 13.62 (br, 2H), 7.29 (s, 2H)

$^{13}$C NMR (125 MHz, DMSO-$d_6$): δ 158.91, 147.04, 118.40

Example 8

At 30° C., 3 mL of tert-butanol was added to barium tert-butoxide (3 equivalents) and then stirred for 5 minutes. 5-Hydroxymethylfurfural (HMF, 0.5 mmol) was added thereto, and the atmosphere was changed to oxygen, and then the mixture was stirred at room temperature for 1 day. To the resulting mixture, a small amount of distilled water was added to terminate the reaction, and the acidity (pH) of the mixture was lowered to 1 with 1N HCl solution, and then the mixture was concentrated. The residue was purified through seed crystals to obtain 2,5-furandicarboxylic acid (FDCA) with 73% yield.

$^{1}$H NMR (500 MHz, DMSO-$d_6$): δ 13.62 (br, 2H), 7.29 (s, 2H)

$^{13}$C NMR (125 MHz, DMSO-$d_6$): δ 158.91, 147.04, 118.40

Example 9

At 25° C., 3 mL of tetrahydrofuran was added to sodium tert-butoxide (3 equivalents) and then stirred for 5 minutes. 5-Hydroxymethylfurfural (HMF, 0.5 mmol) was added thereto, and the atmosphere was changed to oxygen, and then the mixture was stirred at room temperature for 1 day. To the resulting mixture, a small amount of distilled water was added to terminate the reaction, and the acidity (pH) of the mixture was lowered to 1 with 1N HCl solution, and then the mixture was concentrated. The residue was purified through seed crystals to obtain 2,5-furandicarboxylic acid (FDCA) with 81% yield.

$^{1}$H NMR (500 MHz, DMSO-$d_6$): δ 13.62 (br, 2H), 7.29 (s, 2H)

$^{13}$C NMR (125 MHz, DMSO-$d_6$): δ 158.91, 147.04, 118.40

Example 10

At 25° C., 3 mL of 1,4-dioxane was added to sodium tert-butoxide (3 equivalents) and then stirred for 5 minutes. 5-Hydroxymethylfurfural (HMF, 0.5 mmol) was added thereto, and the atmosphere was changed to oxygen, and then the mixture was stirred at room temperature for 1 day. To the resulting mixture, a small amount of distilled water was added to terminate the reaction, and the acidity (pH) of the mixture was lowered to 1 with 1N HCl solution, and then the mixture was concentrated. The residue was purified through seed crystals to obtain 2,5-furandicarboxylic acid (FDCA) with 77% yield.

$^{1}$H NMR (500 MHz, DMSO-$d_6$): δ 13.62 (br, 2H), 7.29 (s, 2H)

$^{13}$C NMR (125 MHz, DMSO-$d_6$): δ 158.91, 147.04, 118.40

Example 11

At 25° C., 3 mL of dichloromethane was added to sodium tert-butoxide (3 equivalents) and then stirred for 5 minutes. 5-Hydroxymethylfurfural (HMF, 0.5 mmol) was added thereto, and the atmosphere was changed to oxygen, and then the mixture was stirred at room temperature for 1 day. To the resulting mixture, a small amount of distilled water was added to terminate the reaction, and the acidity (pH) of the mixture was lowered to 1 with 1N HCl solution, and then the mixture was concentrated. The residue was purified through seed crystals to obtain 2,5-furandicarboxylic acid (FDCA) with 82% yield.

$^{1}$H NMR (500 MHz, DMSO-$d_6$): δ 13.62 (br, 2H), 7.29 (s, 2H)

$^{13}$C NMR (125 MHz, DMSO-$d_6$): δ 158.91, 147.04, 118.40

Example 12

At 25° C., 3 mL of 1,2-dichloroethane was added to sodium tert-butoxide (3 equivalents) and then stirred for 5 minutes. 5-Hydroxymethylfurfural (HMF, 0.5 mmol) was added thereto, and the atmosphere was changed to oxygen, and then the mixture was stirred at room temperature for 1 day. To the resulting mixture, a small amount of distilled water was added to terminate the reaction, and the acidity (pH) of the mixture was lowered to 1 with 1N HCl solution, and then the mixture was concentrated. The residue was purified through seed crystals to obtain 2,5-furandicarboxylic acid (FDCA) with 80% yield.

$^1$H NMR (500 MHz, DMSO-d$_6$): δ 13.62 (br, 2H), 7.29 (s, 2H)

$^{13}$C NMR (125 MHz, DMSO-d$_6$): δ 158.91, 147.04, 118.40

Example 13

At 25° C., 3 mL of chlorobenzene was added to sodium tert-butoxide (3 equivalents) and then stirred for 5 minutes. 5-Hydroxymethylfurfural (HMF, 0.5 mmol) was added thereto, and the atmosphere was changed to oxygen, and then the mixture was stirred at room temperature for 1 day. To the resulting mixture, a small amount of distilled water was added to terminate the reaction, and the acidity (pH) of the mixture was lowered to 1 with 1N HCl solution, and then the mixture was concentrated. The residue was purified through seed crystals to obtain 2,5-furandicarboxylic acid (FDCA) with 78% yield.

$^1$H NMR (500 MHz, DMSO-d$_6$): δ 13.62 (br, 2H), 7.29 (s, 2H)

$^{13}$C NMR (125 MHz, DMSO-d$_6$): δ 158.91, 147.04, 118.40

Example 14

At 25° C., 3 mL of acetonitrile was added to sodium tert-butoxide (3 equivalents) and then stirred for 5 minutes. 5-Hydroxymethylfurfural (HMF, 0.5 mmol) was added thereto, and the atmosphere was changed to oxygen, and then the mixture was stirred at room temperature for 1 day. To the resulting mixture, a small amount of distilled water was added to terminate the reaction, and the acidity (pH) of the mixture was lowered to 1 with 1N HCl solution, and then the mixture was concentrated. The residue was purified through seed crystals to obtain 2,5-furandicarboxylic acid (FDCA) with 75% yield.

$^1$H NMR (500 MHz, DMSO-d$_6$): δ 13.62 (br, 2H), 7.29 (s, 2H)

$^{13}$C NMR (125 MHz, DMSO-d$_6$): δ 158.91, 147.04, 118.40

Example 15

At 25° C., 3 mL of dimethyl sulfoxide was added to sodium tert-butoxide (3 equivalents) and then stirred for 5 minutes. 5-Hydroxymethylfurfural (HMF, 0.5 mmol) was added thereto, and the atmosphere was changed to oxygen, and then the mixture was stirred at room temperature for 1 day. To the resulting mixture, a small amount of distilled water was added to terminate the reaction, and the acidity (pH) of the mixture was lowered to 1 with 1N HCl solution, and then the mixture was concentrated. The residue was purified through seed crystals to obtain 2,5-furandicarboxylic acid (FDCA) with 83% yield.

$^1$H NMR (500 MHz, DMSO-d$_6$): δ 13.62 (br, 2H), 7.29 (s, 2H)

$^{13}$C NMR (125 MHz, DMSO-d$_6$): δ 158.91, 147.04, 118.40

Example 16

At 25° C., 3 mL of N,N-dimethylformamide was added to sodium tert-butoxide (3 equivalents) and then stirred for 5 minutes. 5-Hydroxymethylfurfural (HMF, 0.5 mmol) was added thereto, and the atmosphere was changed to oxygen, and then the mixture was stirred at room temperature for 1 day. To the resulting mixture, a small amount of distilled water was added to terminate the reaction, and the acidity (pH) of the mixture was lowered to 1 with 1N HCl solution, and then the mixture was concentrated. The residue was purified through seed crystals to obtain 2,5-furandicarboxylic acid (FDCA) with 86% yield.

$^1$H NMR (500 MHz, DMSO-d$_6$): δ 13.62 (br, 2H), 7.29 (s, 2H)

$^{13}$C NMR (125 MHz, DMSO-d$_6$): δ 158.91, 147.04, 118.40

Example 17

At 25° C., 3 mL of benzene was added to sodium tert-butoxide (3 equivalents) and then stirred for 5 minutes. 5-Hydroxymethylfurfural (HMF, 0.5 mmol) was added thereto, and the atmosphere was changed to oxygen, and then the mixture was stirred at room temperature for 1 day. To the resulting mixture, a small amount of distilled water was added to terminate the reaction, and the acidity (pH) of the mixture was lowered to 1 with 1N HCl solution, and then the mixture was concentrated. The residue was purified through seed crystals to obtain 2,5-furandicarboxylic acid (FDCA) with 59% yield.

$^1$H NMR (500 MHz, DMSO-d$_6$): δ 13.62 (br, 2H), 7.29 (s, 2H)

$^{13}$C NMR (125 MHz, DMSO-d$_6$): δ 158.91, 147.04, 118.40

Example 18

At 25° C., 3 mL of toluene was added to sodium tert-butoxide (3 equivalents) and then stirred for 5 minutes. 5-Hydroxymethylfurfural (HMF, 0.5 mmol) was added thereto, and the atmosphere was changed to oxygen, and then the mixture was stirred at room temperature for 1 day. To the resulting mixture, a small amount of distilled water was added to terminate the reaction, and the acidity (pH) of the mixture was lowered to 1 with 1N HCl solution, and then the mixture was concentrated. The residue was purified through seed crystals to obtain 2,5-furandicarboxylic acid (FDCA) with 71% yield.

$^1$H NMR (500 MHz, DMSO-d$_6$): δ 13.62 (br, 2H), 7.29 (s, 2H)

$^{13}$C NMR (125 MHz, DMSO-d$_6$): δ 158.91, 147.04, 118.40

Example 19

At 25° C., 3 mL of normal butanol was added to sodium tert-butoxide (3 equivalents) and then stirred for 5 minutes. 5-Hydroxymethylfurfural (HMF, 0.5 mmol) was added

Example 20

At 25° C., 3 mL of tert-amyl alcohol was added to sodium tert-butoxide (3 equivalents) and then stirred for 5 minutes. 5-Hydroxymethylfurfural (HMF, 0.5 mmol) was added thereto, and the atmosphere was changed to oxygen, and then the mixture was stirred at room temperature for 1 day. To the resulting mixture, a small amount of distilled water was added to terminate the reaction, and the acidity (pH) of the mixture was lowered to 1 with 1N HCl solution, and then the mixture was concentrated. The residue was purified through seed crystals to obtain 2,5-furandicarboxylic acid (FDCA) with 80% yield.

$^1$H NMR (500 MHz, DMSO-$d_6$): δ 13.62 (br, 2H), 7.29 (s, 2H)

$^{13}$C NMR (125 MHz, DMSO-$d_6$): δ 158.91, 147.04, 118.40

Example 21

At 25° C., 3 mL of N,N-dimethylacetamide was added to sodium tert-butoxide (3 equivalents) and then stirred for 5 minutes. 5-Hydroxymethylfurfural (HMF, 0.5 mmol) was added thereto, and the atmosphere was changed to oxygen, and then the mixture was stirred at room temperature for 1 day. To the resulting mixture, a small amount of distilled water was added to terminate the reaction, and the acidity (pH) of the mixture was lowered to 1 with 1N HCl solution, and then the mixture was concentrated. The residue was purified through seed crystals to obtain 2,5-furandicarboxylic acid (FDCA) with 77% yield.

$^1$H NMR (500 MHz, DMSO-$d_6$): δ 13.62 (br, 2H), 7.29 (s, 2H)

$^{13}$C NMR (125 MHz, DMSO-$d_6$): δ 158.91, 147.04, 118.40

Example 22

At 25° C., 3 mL of isopropanol was added to sodium tert-butoxide (3 equivalents) and then stirred for 5 minutes. 5-Hydroxymethylfurfural (HMF, 0.5 mmol) was added thereto, and the atmosphere was changed to oxygen, and then the mixture was stirred at room temperature for 1 day. To the resulting mixture, a small amount of distilled water was added to terminate the reaction, and the acidity (pH) of the mixture was lowered to 1 with 1N HCl solution, and then the mixture was concentrated. The residue was purified through seed crystals to obtain 2,5-furandicarboxylic acid (FDCA) with 65% yield.

$^1$H NMR (500 MHz, DMSO-$d_6$): δ 13.62 (br, 2H), 7.29 (s, 2H)

$^{13}$C NMR (125 MHz, DMSO-$d_6$): δ 158.91, 147.04, 118.40

Example 23

At 25° C., 3 mL of normal propanol was added to sodium tert-butoxide (3 equivalents) and then stirred for 5 minutes. 5-Hydroxymethylfurfural (HMF, 0.5 mmol) was added thereto, and the atmosphere was changed to oxygen, and then the mixture was stirred at room temperature for 1 day. To the resulting mixture, a small amount of distilled water was added to terminate the reaction, and the acidity (pH) of the mixture was lowered to 1 with 1N HCl solution, and then the mixture was concentrated. The residue was purified through seed crystals to obtain 2,5-furandicarboxylic acid (FDCA) with 68% yield.

$^1$H NMR (500 MHz, DMSO-$d_6$): δ 13.62 (br, 2H), 7.29 (s, 2H)

$^{13}$C NMR (125 MHz, DMSO-$d_6$): δ 158.91, 147.04, 118.40

Example 24

At 45° C., 3 mL of normal butanol was added to sodium tert-butoxide (3 equivalents) and then stirred for 5 minutes. 5-Hydroxymethylfurfural (HMF, 0.5 mmol) was added thereto, and the atmosphere was changed to oxygen, and then the mixture was stirred at room temperature for 1 day. To the resulting mixture, a small amount of distilled water was added to terminate the reaction, and the acidity (pH) of the mixture was lowered to 1 with 1N HCl solution, and then the mixture was concentrated. The residue was purified through seed crystals to obtain 2,5-furandicarboxylic acid (FDCA) with 87% yield.

$^1$H NMR (500 MHz, DMSO-$d_6$): δ 13.62 (br, 2H), 7.29 (s, 2H)

$^{13}$C NMR (125 MHz, DMSO-$d_6$): δ 158.91, 147.04, 118.40

Example 25

At 45° C., 3 mL of tert-butanol was added to sodium tert-butoxide (3 equivalents) and then stirred for 5 minutes. 5-Hydroxymethylfurfural (HMF, 0.5 mmol) was added thereto, and the atmosphere was changed to oxygen, and then the mixture was stirred at room temperature for 1 day. To the resulting mixture, a small amount of distilled water was added to terminate the reaction, and the acidity (pH) of the mixture was lowered to 1 with 1N HCl solution, and then the mixture was concentrated. The residue was purified through seed crystals to obtain 2,5-furandicarboxylic acid (FDCA) with 82% yield.

$^1$H NMR (500 MHz, DMSO-$d_6$): δ 13.62 (br, 2H), 7.29 (s, 2H)

$^{13}$C NMR (125 MHz, DMSO-$d_6$): δ 158.91, 147.04, 118.40

Example 26

At 55° C., 3 mL of normal butanol was added to sodium tert-butoxide (3 equivalents) and then stirred for 5 minutes. 5-Hydroxymethylfurfural (HMF, 0.5 mmol) was added thereto, and the atmosphere was changed to oxygen, and then the mixture was stirred at room temperature for 1 day. To the resulting mixture, a small amount of distilled water was added to terminate the reaction, and the acidity (pH) of the mixture was lowered to 1 with 1N HCl solution, and then the mixture was concentrated. The residue was purified through seed crystals to obtain 2,5-furandicarboxylic acid (FDCA) with 78% yield.

$^1$H NMR (500 MHz, DMSO-d$_6$): δ 13.62 (br, 2H), 7.29 (s, 2H)

$^{13}$C NMR (125 MHz, DMSO-d$_6$): δ 158.91, 147.04, 118.40

Example 27

At 55° C., 3 mL of tert-butanol was added to sodium tert-butoxide (3 equivalents) and then stirred for 5 minutes. 5-Hydroxymethylfurfural (HMF, 0.5 mmol) was added thereto, and the atmosphere was changed to oxygen, and then the mixture was stirred at room temperature for 1 day. To the resulting mixture, a small amount of distilled water was added to terminate the reaction, and the acidity (pH) of the mixture was lowered to 1 with 1N HCl solution, and then the mixture was concentrated. The residue was purified through seed crystals to obtain 2,5-furandicarboxylic acid (FDCA) with 73% yield.

$^1$H NMR (500 MHz, DMSO-d$_6$): δ 13.62 (br, 2H), 7.29 (s, 2H)

$^{13}$C NMR (125 MHz, DMSO-d$_6$): δ 158.91, 147.04, 118.40

The reaction conditions and results of Examples 1 to 27 are summarized in the following Tables 1 to 3.

TABLE 1

| Example | Reactant | Sodium alkoxide (RO$^-$) | Solvent | Product | Yield (%) |
|---|---|---|---|---|---|
| 1 | HMF | (R = t-Bu) | tert-butanol | FDCA | 98% |
| 2 | | (R = C(CH$_3$)$_2$CH$_2$CH$_3$) | tert-butanol | | 89% |
| 3 | | (R = (CH$_2$CH$_3$)) | tert-butanol | | 75% |
| 4 | | (R = CH$_3$) | tert-butanol | | 56% |

TABLE 2

| Example | Reactant | Metal (M) tert-butoxide | Solvent | Product | Yield (%) |
|---|---|---|---|---|---|
| 5 | HMF | (M = Li) | tert-butanol | FDCA | 88% |
| 6 | | (M = K) | tert-butanol | | 92% |
| 7 | | (M = Mg) | tert-butanol | | 75% |
| 8 | | (M = Ba) | tert-butanol | | 73% |

TABLE 3

| Example | Reactant | Metal alkoxide | Solvent | Product | Yield (%) |
|---|---|---|---|---|---|
| 9 | HMF | NaOtBu | Tetrahydrofuran | FDCA | 81 |
| 10 | | NaOtBu | 1,4-Dioxane | | 77 |
| 11 | | NaOtBu | Dichloromethane | | 82 |
| 12 | | NaOtBu | 1,2-Dichloroethane | | 80 |
| 13 | | NaOtBu | Chlorobenzene | | 78 |
| 14 | | NaOtBu | Acetonitrile | | 75 |
| 15 | | NaOtBu | Dimethyl sulfoxide | | 83 |
| 16 | | NaOtBu | N,N-dimethylformamide | | 86 |
| 17 | | NaOtBu | Benzene | | 59 |

TABLE 3-continued

| Example | Reactant | Metal alkoxide | Solvent | Product | Yield (%) |
|---|---|---|---|---|---|
| 18 | | NaOtBu | Toluene | | 71 |
| 19 | | NaOtBu | Normal butanol | | 85 |
| 20 | | NaOtBu | Tert-amyl alcohol | | 80 |
| 21 | | NaOtBu | N,N-dimethylacetamide | | 77 |
| 22 | | NaOtBu | Isopropanol | | 65 |
| 23 | | NaOtBu | Normal propanol | | 68 |
| 24 | | NaOtBu | Normal butanol | | 87 |
| 25 | | NaOtBu | Tert-butanol | | 82 |
| 26 | | NaOtBu | Normal butanol | | 78 |
| 27 | | NaOtBu | Tert-butanol | | 73 |

As can be seen from the above, according to the present invention, it is possible to prepare highly pure 2,5-furandicarboxylic acid (FDCA) more efficiently and economically through a chemoselective oxidation reaction based on eco-friendly protocols of alkali metal (or alkaline-earth metal) compound promotor and oxygen (or air) oxidizing agent.

The invention claimed is:

1. A method for preparing 2,5-furandicarboxylic acid from 5-hydroxymethylfurfural through a chemoselective oxidation reaction, the method comprising:
   (1) mixing a promotor which is an alkali metal compound and a solvent comprising butanol at a temperature of from 25° C. to 30° C.; and
   (2) adding 5-hydroxymethylfurfural to the resulting mixture of the above step (1), and then conducting a chemoselective oxidation reaction with using oxygen or air as an oxidizing agent,
   wherein the alkali metal compound is represented by the following Formula 1:

MOR     [Formula 1]

wherein M is an alkali metal; and R is a ($C_4$-$C_6$) alkyl group.

2. The method for preparing 2,5-furandicarboxylic acid of claim 1, wherein the alkali metal is lithium, sodium, potassium, rubidium, cesium or a combination thereof.

3. The method for preparing 2,5-furandicarboxylic acid of claim 1, wherein no transition metal catalyst is used.

4. The method for preparing 2,5-furandicarboxylic acid of claim 1, wherein the chemoselective oxidation reaction is conducted at a temperature of from 20° C. to 100° C.

5. The method for preparing 2,5-furandicarboxylic acid of claim 1, wherein the chemoselective oxidation reaction is conducted at 1 to 10 atmospheres.

* * * * *